United States Patent [19]

Swindell et al.

[11] Patent Number: 6,072,060

[45] Date of Patent: *Jun. 6, 2000

[54] SYNTHESIS OF TAXOL, TAXOL ANALOGS AND THEIR INTERMEDIATES WITH VARIABLE A-RING SIDE CHAIN STRUCTURES AND COMPOSITIONS THEREOF

[75] Inventors: Charles S. Swindell, Merion, Pa.; Nancy Krauss, Sunnyvale, Calif.

[73] Assignee: Bryn Mawr College, Bryn Mawr, Pa.

[*] Notice: This patent is subject to a terminal disclaimer.

[21] Appl. No.: 09/253,325

[22] Filed: Feb. 19, 1999

Related U.S. Application Data

[63] Continuation of application No. 08/483,083, Jun. 7, 1995, Pat. No. 5,939,566, and a division of application No. 08/357,507, Dec. 15, 1994, Pat. No. 5,770,745, and a continuation of application No. 08/015,095, Feb. 5, 1993, abandoned.

[51] Int. Cl.$^7$ .................................................. C07D 304/14
[52] U.S. Cl. ............................ 549/510; 549/511; 560/23; 560/27; 560/39
[58] Field of Search ...................... 549/510, 511; 560/23, 27, 39

[56] References Cited

U.S. PATENT DOCUMENTS

| | | | |
|---|---|---|---|
| 4,814,470 | 3/1989 | Colin et al. ............................... | 514/449 |
| 4,857,653 | 8/1989 | Colin et al. ............................... | 549/511 |
| 4,924,011 | 5/1990 | Denis et al. ............................... | 549/510 |
| 4,924,012 | 5/1990 | Colin et al. ............................... | 549/510 |
| 5,015,744 | 5/1991 | Holton ..................................... | 549/510 |
| 5,136,060 | 8/1992 | Holton ..................................... | 549/510 |

FOREIGN PATENT DOCUMENTS

| | | |
|---|---|---|
| 0 400 971 | 5/1990 | European Pat. Off. . |
| 0 528 729 A1 | 8/1992 | European Pat. Off. . |
| 2 687 150 | 2/1992 | France . |
| WO 91/13066 | 9/1991 | WIPO . |

OTHER PUBLICATIONS

"New and Efficient Approaches to the Semisynthesis of Taxol and its C–13 Side Chain Analogs, by Means of B–Lactam Synthon Method", Ojima et al, *Tetrahedron*, vol. 48, No. 34, pp. 6985–7012 1991.

"Improved Protection and Esterification of a Precursor of the Taxotere and Taxol Side Chains", Commercon et al, *Tetrahedron*, vol. 33, No. 33, pp. 5185–5188, 1992.

"Highly Stereocontrolled and Efficient Preparation of the Protected, Esterification–Ready Docetaxel (Taxotere) Side Chain", Kanazawa et al, Org. Chem., vol. 59, No. 6, pp. 1238–1240, 1994.

"Enantioselective Synthesis of B–Amino Acids", edited by E. Juaristi, *Viley–Vch*, 1997.

"Biologically Active Taxol Analogues with Deleted A–Ring Side Chain Substituents and Variable C–2' Configurations", Swindell et al, J. of Med. Chem., 1991, vol. 34, No. 3, pp. 1176–1184.

*Primary Examiner*—Ba K. Trinh
*Attorney, Agent, or Firm*—Timothy J. Martin; Michael R. Henson; Mark H. Weygandt

[57] ABSTRACT

An efficient protocol for the synthesis of taxol, taxol analogs and their intermediates is described. The process incudes the attachment of the taxol A-ring side chain to baccatin III and for the synthesis of taxol and taxol analogs with variable A-ring side chain structures. A rapid and highly efficient esterification of O-protected isoserine and 3-phenylisoserine acids having N-benzyoloxycarbonyl groups to the C-13 hydroxyl of 7-O-protected baccatin III is followed by a deprotection-acylation sequence to make taxol, cephalomanninne and various analogs, including photoaffinity labeling candidates.

24 Claims, No Drawings

SYNTHESIS OF TAXOL, TAXOL ANALOGS AND THEIR INTERMEDIATES WITH VARIABLE A-RING SIDE CHAIN STRUCTURES AND COMPOSITIONS THEREOF

This is a continuation of Ser. No. 08/483,083 filed Jun. 7, 1995, now U.S. Pat. No. 5,939,566, which is also a division of application Ser. No. 08/357,507 filed on Dec. 15, 1994 now U.S. Pat. No. 5,770,743 which is a continuation of Ser. No. 08/015,095 filed Feb. 5, 1993 now abandoned.

FIELD OF THE INVENTION

The present invention concerns the synthesis production of taxol, taxol analogs and their intermediates.

BACKGROUND OF THE INVENTION

Taxol is a naturally occurring taxane diterpenoid that has exhibited significant clinical activity as an antineoplastic agent with considerable potential for further development. The widespread treatment of candidates for taxol therapy is limited by the current scarcity of the drug. The low abundance of taxol in its natural source, the bark of the slow-growing Pacific yew, makes the long term prospects for the availability of taxol through isolation discouraging. Taxol has the general formula and a corresponding numbering system, as shown below:

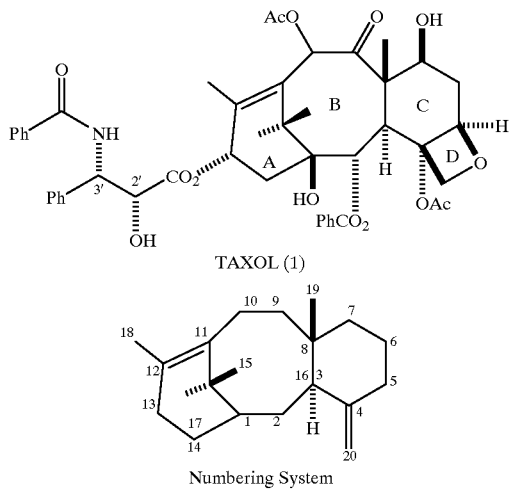

TAXOL (1)

Numbering System

Among the solutions to the taxol supply problem addressable by organic chemists is the partial synthesis of the drug, or of clinically effective analogs, by the attachment to naturally derived substances like baccatin III of the A-ring side chain that protrudes from the C-13 position. The preparation of taxol and its analogs is known. For example, U.S. Pat. No. 4,924,011, issued May 8, 1990 to Denis et al discloses the process for preparing taxol by the condensation of a (2R, 3S) side chain acid with a taxane derivative, followed by the removal of various groups protecting the hydroxyl groups. U.S. Pat. No. 4,924,012, issued May 8, 1990 to Colin et al discloses a process for preparing derivatives of baccatin III and of 10-deacetyl-baccatin III, by condensation of an acid with a derivative of baccatin III or of 10-deacetylbaccatin III, with the subsequent removal of protecting groups by hydrogen. Several syntheses of TAXO-TERE® (Registered to Rhone-Poulenc Sante) and related compounds have been reported in the *Journal of Organic Chemistry:* 1986, 51, 46; 1990, 55, 1957; 1991, 56, 1681; 1991, 56, 6939; 1992, 57, 4320; 1992, 57, 6387; and 993, 58, 255; also, U.S. Pat. No. 5,015,744 issued May 14, 1991 to Holton describes such a synthesis.

The most straightforward implementation of partial synthesis of taxol requires convenient access to chiral, non-racemic side chain and derivatives, an abundant natural source of baccatin III or closely related diterpenoid substances, and an effective means of joining the two. Of particular interest then is the condensation of Baccatin III and 10-deacetyl Baccatin III of the formula:

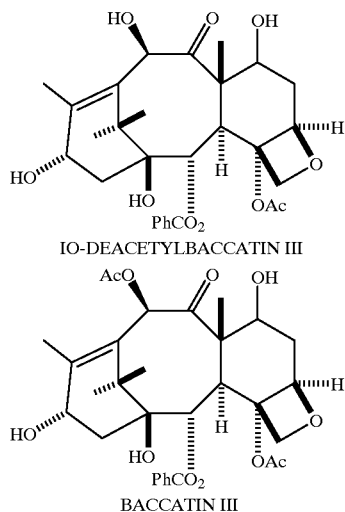

IO-DEACETYLBACCATIN III

BACCATIN III with the side chain:

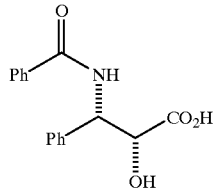

However, the esterification of these two units is difficult because of the hindered C-13 hydroxyl of baccatin III located within the concave region of the hemispherical taxane skeleton. For example, Greene and Gueritte-Voegelein reported only a 50% conversion after 100 hours in one partial synthesis of taxol. *J. Am. Chem. Soc.,* 1988, 110, 5917. The Holten patent addresses one method of more efficient synthesis.

Still, a need exists for further efficient protocols for the attachment of the taxol A-ring side chain to the taxane skeleton (e.g., baccatin III) and for the synthesis of taxol, taxol analogs and their intermediates with variable A-ring side chain structures.

SUMMARY OF THE INVENTION

Accordingly, it is a general object of this invention to provide a new, useful and efficient protocol for the attachment of the taxol A-ring side chain to the taxane skeleton for the synthesis of taxol, taxol analogs and their intermediates with variable A-ring side chain structures which overcomes the disadvantages of the prior art.

Another object of the present invention is the attachment of the taxol A-ring side chain to baccatin III to synthesize taxol, taxol analogs and their intermediates with variable A-ring side chain structures.

It is a further object of this invention to provide a rapid and highly efficient esterification of O-protected isoserine and 3-phenylisoserine acids having N-benzyloxycarbonyl groups to the C-13 hydroxyl of 7-O-protected baccatin III.

It is another object of this invention to provide a deprotection-acylation sequence to the foregoing, to provide taxol, cephalomannine, 10-acetyl TAXOTERE® and various analogs, including photoaffinity labeling candidates.

In its broad form, the present invention provides a chemical process useful in the production of taxol, taxol analogs and their intermediates. This process includes the step of condensing a compound of the general formula:

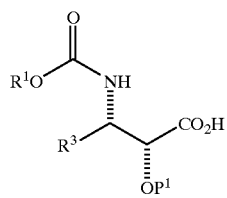

with a taxane of the general structure:

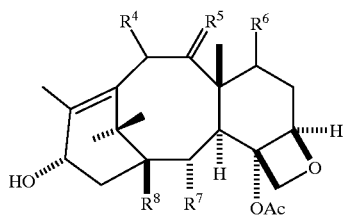

to give an intermediate of the general structure:

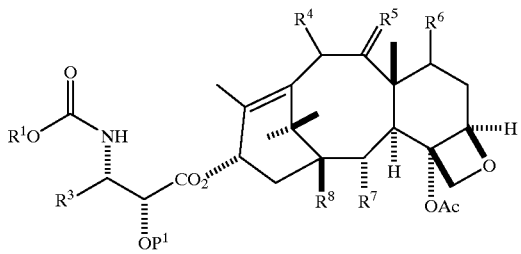

wherein:
$R^1$=alkyl, olefinic or aromatic group or $PhCH_2$
$R^3$=hydrogen, alkyl, olefinic group, aromatic group or Ph
$R^4$=hydrogen, oxygen group or acetoxy
$R^5$=hydrogen, oxygen group or carbonyl
$R^6$=hydrogen, oxygen group or acetoxy
$R^7$=hydrogen, oxygen group, benzoyloxy or aroyloxy
$R^8$=hydrogen or hydroxyl group
$P^1$=hydroxyl protecting group.

Various substitutions according to the general process are contemplated, especially those wherein $R^1$ is $PhCH_2$, $R^3$ is Ph, $R^4$ is AcO, $R^5$ is double bonded O, $R^6$ is OH, $R^7$ is $PhCO_2$ and $R^8$ is OH. The general process may be continued by the step of replacing $R^1O$ and $P^1$ in the intermediate to produce a compound of the general structure:

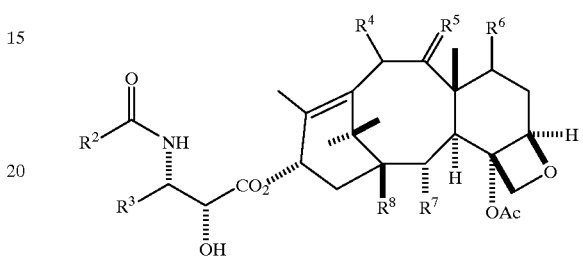

wherein $R^2$=hydrogen, alkyl, olefinic, aromatic, oxygen, nitrogen, sulfur or Ph group Again, various preferred substitutions are contemplated. The reaction may take place in the presence of an aromatic solvent, an activating agent and possibly a condensing agent. A preferred reaction temperature of 70°–75° C. is disclosed.

DETAILED DESCRIPTION OF THE INVENTION

The present invention concerns a chemical process for the efficient production of taxol, taxol analogs and their intermediates. This can be accomplished by the attachment of the taxol A-ring side chain to baccatin III. This allows for the synthesis of taxol, taxol analogs and their intermediates with variable A-ring side chain structures. This invention further concerns the rapid and efficient esterification of O-protected isoserine and 3-phenylisoserine acids having N-benzyloxycarbonyl groups to the C-13 hydroxl of 7-O-protected baccatin III.

Isoserine Analogs

Previously we reported partial syntheses of taxol analogs with deleted A-ring side chain substituents through a variant of the Greene, Gueritte-Voegelein protocol. Swindell et al, *J. Med. Chem*, 1991, 34, 1176. The Greene, Gueritte-Voegelein protocol may be summarized:

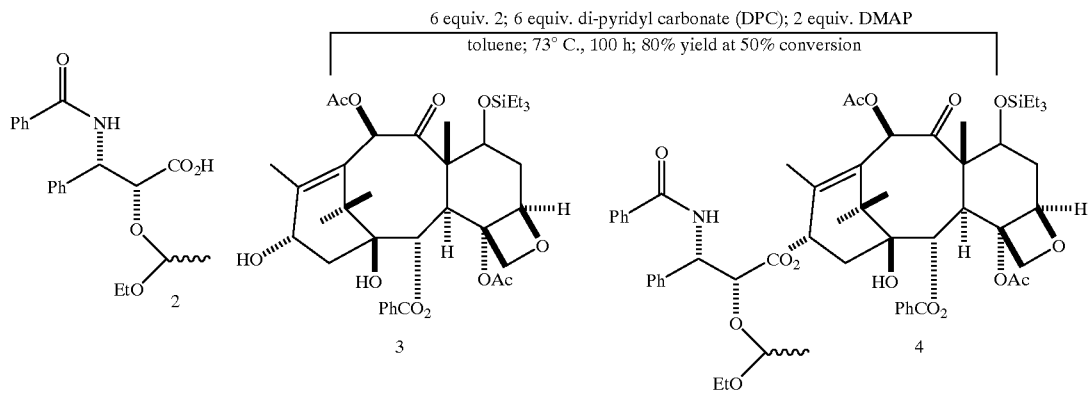

Our findings, according to the generalized reaction:

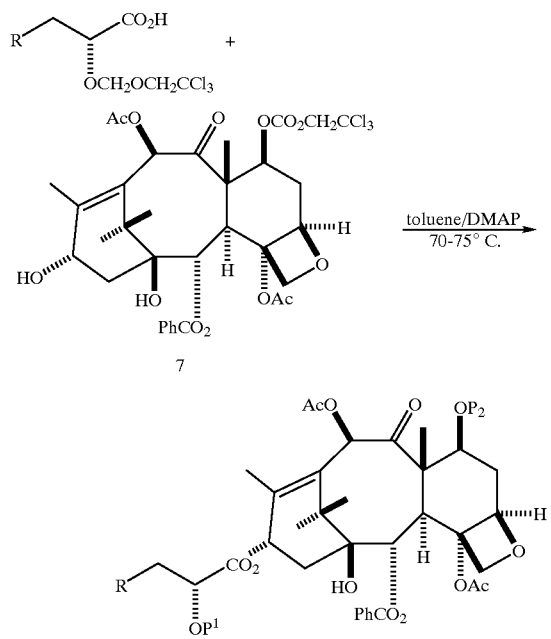

wherein $P^1$ is a hydroxy-protecting group, e.g., (trichloro)ethoxymethyl, methoxymethyl, 1-ethyoxymethyl, benzyloxymethyl, 2-(trimethylsilyl)ethoxymethyl, tetrahydropyranyl and allyloxymethyl; and $P^2$ is a hydroxy-protecting group, e.g., 3, 3, 3-(trichloro)ethyoxycarbonyl, trialkylsilyl, allyloxycarbonyl and benzyloxycarbonyl). can be summarized in the following Table 1:

TABLE 1

(Lactate, Phenyllactate and Isoserine Side Chain Esterifications)

| R | Equivalents Acid | Coupling Reagent | Time | Product | Yield(%) |
|---|---|---|---|---|---|
| H (8)[a] | 6 | DPC | 24 h | 12 | 53[a] |
| Ph (9)[a] | 6 | DPC | 48 h | 13 | 37[b] |
| PhCONH (10)[a] | 6 | DPC | 6 h | 14 | 87 |

TABLE 1-continued (Lactate, Phenyllactate and Isoserine Side Chain Esterifications)

| R | Equivalents Acid | Coupling Reagent | Time | Product | Yield(%) |
|---|---|---|---|---|---|
| PhCH$_2$OCONH (11)[c] | 6 | DCC | 15 m | 15 | 97 |
|  | 2.2 | DCC | 30 m |  | 100 |

[a]See, Swindell et al, J. Med. Chem., 1991, 34, 1176.
[b]Yield includes subsequent deprotection of 2' and 7-hydroxyl groups.
[c]This work.

One of our goals in carrying out that work was the discovery of biologically active taxol analogs with structurally simpler side chains that might be attached to baccatin III through conventional esterification chemistry more efficiently than can the taxol side chain. We detected for the lactate and phenyllactate analogs (12 and 13) a straightforward relationship between side chain complexity and side chain attachment rate and efficiency. However, we were surprised to find that N-(benzoyl)isoserine side chain acid 10, arguably as sterically demanding as phenyllactic acid 9, was esterified to 7-O-protected baccatin III 7, Magri et at, *J. Org. Chem.*, 1986, 51, 3239, with a remarkably high rate and efficiency. We proposed the intervention of a dihydrooxazine of the formula:

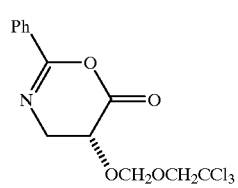

formed from the preliminary intramolecular acylation of the benzamide carbonyl oxygen. We suggested: (i) that cyclic acylating agent 16, because of its limited steric requirement, would be particularly reactive toward the baccatin III C-13 hydroxyl; and (ii) that more complex dihydrooxazine analogs to 16 might offer a general solution to the taxol side chain attachment problem.

Owing to the central position of the A-ring side chain in taxol's structure activity profile and consequently in its recognition by the microtubular binding site(s), photoaffinity labeling taxol analogs with photo functionality in the side chain would be valuable in the investigation of the chemical details of the taxol-microtubule interaction. Thus we were motivated to pursue the involvement of benzyl urethane-protected side chain acid 11 out of the expectation that an N-deprotection-acylation sequence following side chain attachment would provide access to photolabelling agents with late-stage incorporation of both photolabile functionality and radiolabel.

When mixtures of 7, 11, dicyclohexylcarbodiimide (DCC), and 4-(dimethylamino)pyridine (DMAP) in toluene were warmed at concentrations that allow the comparison of the esterifications collected in Table 1, side chain attachments more rapid and higher yielding than those with benzamide 10 resulted. On the presumption that dihydrooxazine of the formula:

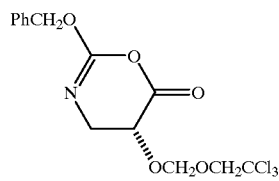

17 intervenes and that its formation is the rate-limiting event—no intermediate could be detected in this esterification—the higher reactivity of 11 is a consequence of the higher nucleophilicity of its urethane carbonyl oxygen. This feature allows a considerable reduction in the excess in which the side chain acid is employed.

Zinc-induced removal of the trichloroethoxy-based O-protecting groups led to the taxol analog:

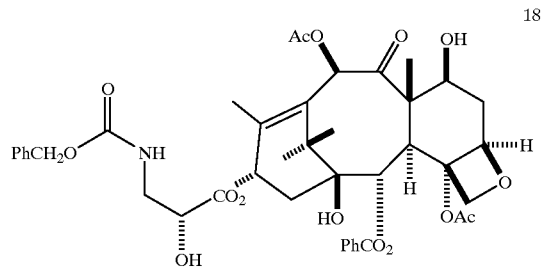

18

Subsequent hydrogenolytic removal of the benzyl urethane in a solution containing trifluoroacetic acid (TFA), and selective acylation of the amino group according to the reaction:

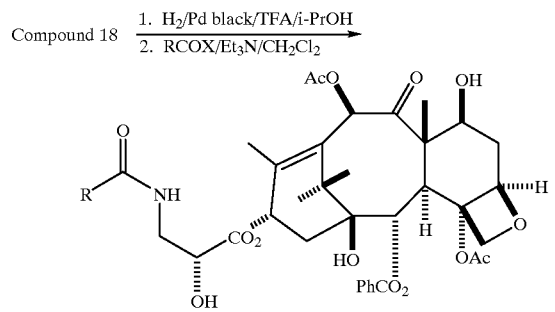

produced the taxol analogs shown in Table 2.

TABLE 2

| | (Deprotection-Acylation of Compound 18) | |
|---|---|---|
| RCO | Product | Overall Yield (%) |
| 4-azidobenzoyl | 19 | 79[a] |
| | | 75[b] |
| 4-(trifluoromethyl)benzoyl | 20 | 52[a] |
| 2-naphthoyl | 21 | 64[a] |
| hexanoyl | 22 | 64[a] |
| pivaloyl | 23 | 79[a] |
| cyclohexylcarbonyl | 24 | 50[a] |
| 1-adamantylcarbonyl | 25 | 70[a] |
| t-butoxycarbonyl | 26 | 89[c] |

[a]Prepared using the acid chloride.
[b]Prepared using excess amine and 4-azidobenzoic acid N-hydroxysuccinimide ester.
[c]Prepared using di-t-butyldicarbonate.

Benzyl protecting groups are useful in this context since the taxane bridgehead olefin is known to be resistant to hydrogenation. Baxter et al, *J. Chem. Soc.*, 1962, 2964.

3-Phenylisoserine Analogs

While the enhanced rate of attachment of side chain 11 was a convenience in the preparation of the above analogs, a similar improvement in the esterification to the baccatin III C-13 hydroxyl of the more complex N-acyl-3-phenylisoserine side chain characteristic of taxol would have a more dramatic impact. We investigated 3-phenylisoserine side chain esterifications according to the scheme:

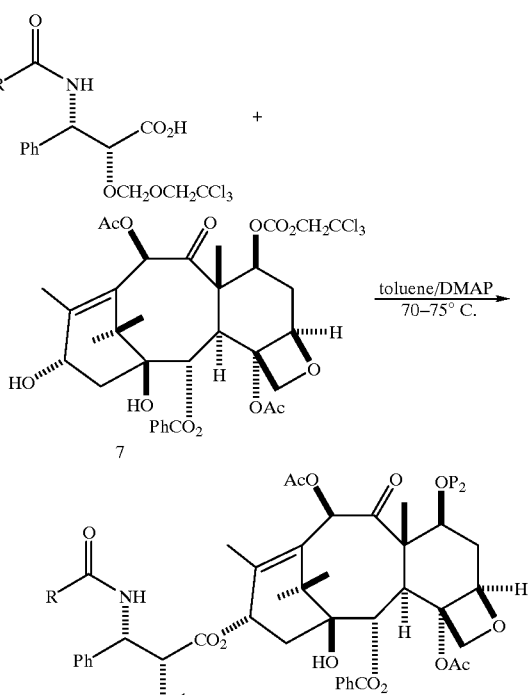

with the results being summarized in the following Table 3:

TABLE 3

(3-Phenylisoserine Side Chain Esterifications)

| R | Equivalents Acid | Coupling Reagent | Time | Product | Yield(%) |
|---|---|---|---|---|---|
| Ph(27) | 10 | DPC | 36 h | 29 | 50 (96[a]) |
| | 6 | DPC | 48 h | | 0 |
| PhCH$_2$O (28) | 10 | DPC | 36 h | 30 | 50 (78[a]) |
| | 6 | DCC | 1 h | | 94 |
| | 3.9 | DCC | 2 h | | 78 (84[a]) |

[a]Based on recovered 7.

Unfortunately, the low rate of esterification in the Greene, Gueritte-Voegelein taxol partial synthesis and our own similar observation for side chain acid 27 suggested that dihydrooxazines were not accessed rapidly from side chain acids bearing the combination of N-benzoyl and 3-phenyl substituents. Furthermore, no rate enhancement in the esterification of benzyl urethane acid 28 prepared through a combination of the Greene (Denis et al, *J. Org. Chem.*, 1990, 55, 1957) and Jacobsen (Deng et al, *J. Org. Chem.*, 1992, 57, 4320) taxol side chain syntheses was observed when DPC served as the carboxyl activation reagent (again, the esterifications summarized in Table 3 are comparable). However, 28 in combination with DCC led to the same high rates and yields witnessed above. That it is the combination of the more nucleophilic urethane oxygen and DCC as the carboxyl activation reagent that is particularly effective, presumably in causing the in situ formation of:

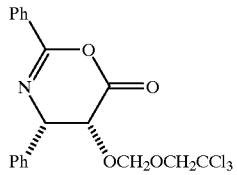

31 was demonstrated by the failure of DCC to cause the efficient attachment of 27. The formation of 31, if relevant, must be rate limiting since no intermediate could be detected in esterifications with 28. In the side chain attachments we have investigated to date, DPC, introduced by Greene and Gueritte-Voegelein for taxol side chain esterification, has been the most effective reagent when the side chain nitrogen bears the benzoyl group, whereas DCC has been the most effective at mediating the rapid esterification of benzyl urethane-containing side chain acids.

Zinc treatment of 30 led to 33. A series of hydrogenolysis-acylation experiments gave taxol, cephalomannine, 10-acetyl TAXOTERE® and the remaining analogs listed in Table 4 which reactions are generalized by the scheme:

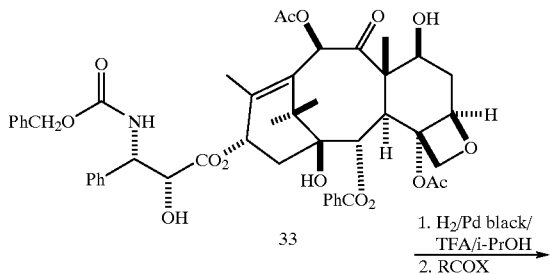

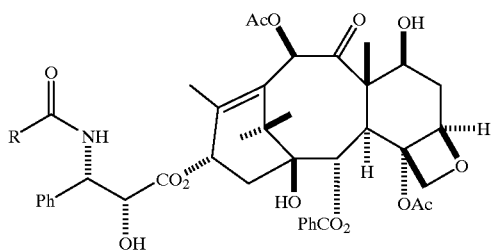

(wherein X is any leaving group, e.g., —Cl, OCO$_2$(CH$_3$)$_3$, or

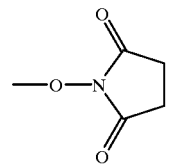

and i-PrOH is isopropyl alcohol)

TABLE 4

(Deprotection-Acylation of 33)

| RCO | Product | Overall Yield (%) |
|---|---|---|
| benzoyl | taxol | 90[a] |
| tigloyl | cephalomannine | 81[a] |
| t-butoxycarbonyl | 10-acetyl Taxotere ® | 94[b] |
| 4-azidobenzoyl | 34 | 71[a] |
| | | 79[c] |
| 4-(trifluoromethyl)benzoyl | 35 | 86[a] |
| 4-bromobenzoyl | 36 | 76[a] |
| 4-(acetyl)benzoyl | 37 | 67[a] |
| 4-(benzoyl)benzoyl | 38 | 66[a] |
| salicyl | 39 | 51[d] |

[a]Prepared using the acid chloride.
[b]Prepared using di-t-butyldicarbonate.
[c]Prepared using excess amine and 4-azidobenzoic acid N-hydroxysuccinimide ester.
[d]Prepared using salicylic acid N-hydroxysuccinimide ester.

The amino triol encountered after the hydrogenolysis of 33 is particularly prone to O-acylation at the C-2' site. For example, in the preparation of cephalomannine, significant O-acylation occurred even when the N-hydroxysuccinimide ester of tiglic acid was employed. Furthermore, the use of acid chlorides in triethylamine-methylene chloride solution, even at low temperature, was not reliably selective for all the analogs of interest. Surprisingly, the best conditions for effecting selective amino acylation involved the acid chlorides in pyridine solution with DMAP catalysis at room temperature.

While it was gratifying to achieve an efficient partial synthesis of taxol, the preparation of the photoaffinity labeling azide analog 34 underscores the utility of this methodology. In our hands, the application of the Greene, Gueritte-Voegelein esterification to the preparation of 34 from an O-protected side chain acid bearing an N-p-azidobenzoyl group failed owing to the thermal instability of the azide moiety. Through the chemistry described herein, 34 is available in good yield through a sequence amenable to the preparation of radiolabeled material.

C-2' And C-7 Hydroxyl Protection

Several hydroxyl protection protocols were investigated during this work. Any in situ carboxyl activation approach to taxol and taxol analog partial synthesis demands that these protecting groups be conveniently acid stable. Among those that failed to meet this standard in our hands were triethylsilyl for the C-2' hydroxyl of the isoserine side chain, and ethoxy-ethyl for this hydroxyl in the 3-phenylisoserine side chain type. Generally, we found that the acid stability of the side chain hydroxyl protecting group in the 3-phenylisoserine side chain acid needed to be greater than that required in the simpler isoserine acid. Likewise, the removal of acid-labile hydroxyl protecting groups after esterification was more difficult for the isoserine taxol analogs. For that reason, ethoxyethyl was unsuitable for the latter side chain category. Among the side chain hydroxyl masking groups that complicated or prevented the esterifications were triisopropylsilyl and trichloroethoxycarbonyl. The benzyloxymethyl group was quite acceptable for the isoserine side chain, but could not be removed from the more encumbered C-2' hydroxyl in the attached 3-phenylisoserine side chain. Out of this experience we established that the known trichloroethoxymethyl protecting group and the known trichloroethoxycarbonyl group were good protecting groups for the C-2' and the C-7 hydroxyl. These devices are robust toward the side chain carboxylic acid during esterification reactions, and are both removable in a single reductive operation that is compatible with the functionality of 18, 33, taxol, and related complex taxanes.[17]

A simple and effective sequence for the preparation of taxol and analogs has been developed that is based on the rapid and high yielding esterification of O-protected isoserine and 3- phenylisoserine side chain acids incorporating N-benzyloxycarbonyl functionality to the sterically hindered C-13 hydroxyl of 7-O-protected baccatin III. We believe that dihydrooxazines like 17 and the compound:

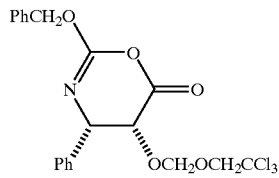

32 formed in situ, intervene. Deprotection of the esterification products and acylation of the side chain amino group provide the target substances. From baccatin III, five steps are required overall.

Before this work, the most effective methods for the attachment of the taxol side chain to the baccatin III C-13 hydroxyl required the independent formation of β-lactam and dihydrooxazine acylating agents. With the present methodology for in situ dihydrooxazine generation from suitable protected side chain acids, the several asymmetric syntheses of the taxol side chain that have been reported become especially useful for the partial synthesis of taxol and related drugs.

Generalized Formula

Taxol, Taxol Analogs and Their Intermediates

The chemical process of the present invention for the production of taxol, taxol analogs and their intermediates may be generalized, then, as the condensation of a compound of the general formula:

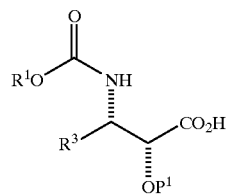

with a taxane of the general structure:

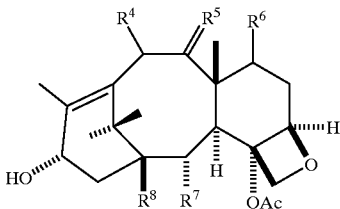

to give an intermediate of the general structure:

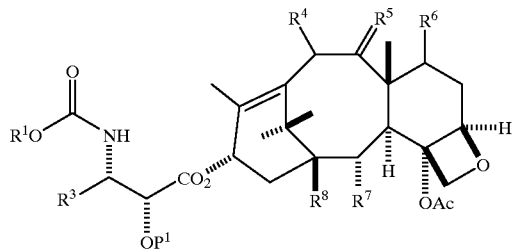

wherein:

$R^1$=alkyl, olefinic or aromatic group or $PhCH_2$ $R^3$=hydrogen, alkyl, olefinic, aromatic or Ph $R^4$=hydrogen, oxygen group or acetoxy $R^5$=hydrogen, oxygen group or carbonyl $R^6$=hydrogen, oxygen group or acetoxy $R^7$=hydrogen, oxygen group, benzoyloxy or aroyloxy $R^8$=hydrogen or hydroxyl group $P^1$=hydroxyl protecting group.

In this general process, certain more specific reactions include those where: (i) $R^1$ is $PhCH_2$, $R^3$ is Ph and $P^1$ is $CH_2OCH_2CCl_3$; (ii) $R^1$ is $PhCH_2$, $R^3$ is Ph, $R^4$ is AcO, $R^5$ is double bonded O, $R^6$ is $OCO_2CH_2CCl_3$, $R^7$ is $PhCO_2$, $R^8$ is OH and $P^1$ is $CH_2OCH_2CCl_3$; (iii) $R^1$ is $PhCH_2$, $R^3$ is Ph, $R^4$ is AcO, $R^5$ is double bonded O, $R^6$ is OH, $R^7$ is $PhCO_2$, $R^8$ is OH and $P^1$ is H; and (iv) $R^3$ is Ph, $R^4$ is AcO, $R^5$ is double bonded O, $R^6$ is $OP^2$, $R^7$ is $PhCO_2$, $R^8$ is OH and wherein $P^2$ is a hydroxl-protecting group.

The general process set forth above can be continued with the further step of replacing $R^1O$ and $P^1$ to give a compound of the general structure:

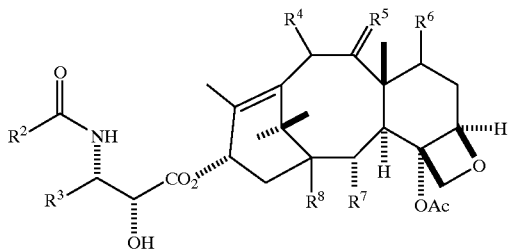

wherein $R^2$=hydrogen, alkyl, olefinic, aromatic, oxygen, nitrogen or sulfur group or Ph group Alternatively, the general process set forth above can be more specific in the following ways: (i) $R^1$ is an alkyl, olefinic or aromatic group, $R^3$ is Ph, $R^4$ is AcO, $R^5$ is double bonded O, $R^6$ is $OP^2$, $R^7$ is $PhCO_2$, $R^8$ is OH, and $P^2$ is a hydroxyl-protecting groups, and including the step of replacing $R^1O$ with Ph and P and $P^2$ with hydrogen to produce taxol; (ii) $R^1$ is $PhCH_2$, $P^1$ is $CH_2OCH_2CCl_3$ and $P^2$ is $CO_2CH_2CCl_3$ and wherein the step of replacing $R^1O$ with Ph is accomplished by exchanging the $PhCH_2OC$=O group for a PhC=O group; (iii) $R^1$ is an alkyl, olefinic or aromatic group, $R^3$ is hydrogen, alkyl, olefinic or aromatic group, $R^4$ is AcO, $R^5$ is double bonded O, $R^6$ is $OP^2$, $R^7$ is $PhCO_2$, $R^8$ is OH and $P^2$ is a hydroxyl-protecting group, and including the step of replacing $R^1O$ with Ph and $P^1$ and $P^2$ with hydrogen to produce a taxol analog; and (iv) $R^1$ is $PhCH_2O$, $R^3$ is Ph, $R^4$ is AcO, $R^5$ is double bonded O, $R^6$ is $OP^2$, $R^7$ is $PhCO_2$, $R^8$ is OH and $P^2$ is a hydroxyl protecting group and wherein the condensation is a 3-phenylisoserine side chain esterification conducted in the presence of an aromatic solvent and an activating agent.

In the latter case (iv), $P^2$ may be $CH_2OCH_2CCl_3$ and $P^2$ may be $CO_2CH_2CCl_3$. Here, the activating agent is chosen from dialkylaminopyridines, such as 4-(dimethylamino) pyridine. The organic solvent is chosen from benzene, toluene, xylenes, ethylbenzene, iospropylbenzene and chlorobenzene. The reaction is best performed at a temperature of between approximately 70–75° C. The esterification is performed in the presence of a condensing agent, and this condensing agent may be selected from the group consisting of di-cyclohexyl-carbodiimide and di-2-pyridyl carbonate. Finally, the reaction of (iv) may be performed in the presence of a condensing agent selected from the group consisting of di-cyclohexyl-carbodiimide and di-2-pyridyl carbonate and an activating agent is 4-(dimethylamino) pyridine.

In addition, the chemical process for the preparation of taxol analogs may also be generalized by the process comprising the following steps:

converting 10-deacetyl baccatin III to:

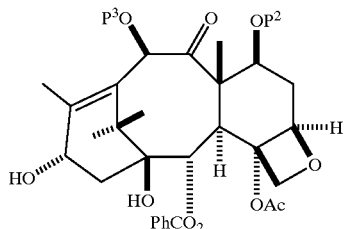

then to:

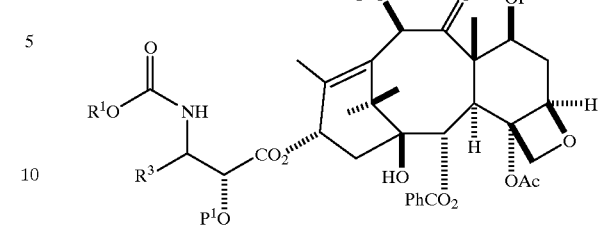

by condensation with:

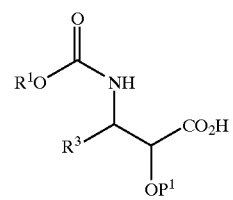

conversion to:

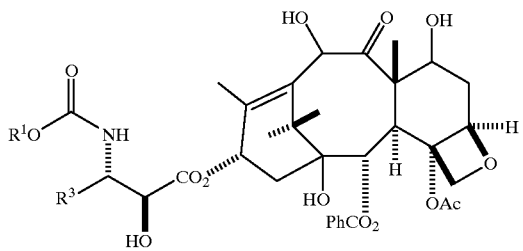

followed by conversion to:

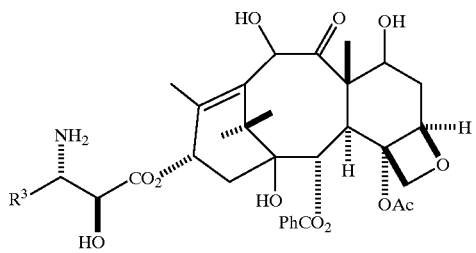

and then ultimately taxol analogs of the following type:

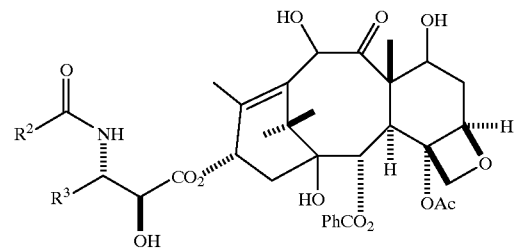

wherein:
  $R^1$=alkyl, olefinic, or aromatic group
  $R^2$=hydrogen, alkyl, olefinic, aromatic, oxygen, nitrogen, or sulfur groups $R^3$=hydrogen, alkyl, olefinic, or aromatic group
$P^1$, $P^2$ and $P^3$=$CO_2CH_2CCl_3$ or other hydroxyl-protecting group

EXPERIMENTAL SECTION

Baccatin III was prepared, as described by Magri et al, *J. Org. Chem.*, 1986, 51, 3239, by degradation of a taxol-cephalomannine mixture provided by Dr. Kenneth Snade, National Cancer Institute, National Institutes of Health. It was converted to baccatin III 7-trichloroethyl carbonate (7) according to this procedure. Reactions requiring anhydrous conditions and inert atmospheres were performed in flame-dried glassware under nitrogen using anhydrous solvents. $^1H$ and $^{13}C$ NMR spectra of $CDCl_3$ solutions were recorded at 300 MHz and 75 MHz, respectively, using tetramethylsilane ($^1H$ δ=O ppm), residual chloroform (H δ=7.27 ppm), or $CDECl_3$ ($^{13}C$ δ=77 ppm) as the internal standard. For $^{13}C$ NMR spectra, degrees of proton substitution were assigned with the aid of 1F DEPT experiments. High Performance Liquid Chromatography (HPLC) was carried out with a Waters brand instrument on a 3.9 mm×15 cm NovaPak brand $D_{18}$ column, or on a 7.8×30 cm NovaPak $C_{13}$ column, employing UV detection at 254 nanometers (nm) Otherwise, chromatography was performed on silica gel. High resolution mass spectral determinations were performed at the Mass Spectrometry Laboratory, Department of Chemistry, University of Pennsylvania, Philadelphia, Pa., USA.

Simple isoserine side claims were prepared in a standard manner and included: (i) (2R) -N-(Benzyloxycarbonyl)-O-(trichloroethoxymethyl)-isoserine (Compound 11); (ii) Baccatin III Ester 15 (Compound 15 formed from Compound 11); and (iii) Baccatin III Ester 18 (Compound 18 formed from Compound 15).

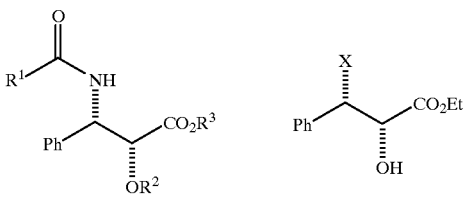

43 X = $N_3$
44 X = $NH_2$
45 $R^1$ = $PhCH_2O$, $R^2$ = H, $R^3$ = Et
46 $R^1$ = $PhCH_2O$, $R^2$ = $CH_2OCH_2CCl_3$, $R^3$ = $E^t$

Compound 28, (2R,3S)-N-Benzyloxycarbonyl-O-(trichloroethoxymethyl)-3-phenylisoserine, was prepared. Here, a solution of 3.12 g (16.3 mmol) (2R,3R)-ethyl 3-phenylglycidate, 13.5 mL methyl formate, and 5.28 g (81.5 mmol) sodium azide in 81 mL 8:1 95% ethanol-water was heated to 50° C. for 45 hours. The reaction mixture was partitioned between water and diethyl ether, the aqueous layer was extracted with diethyl ether, and the organic layers were combined, dried ($MgSO_4$), filtered concentrated. Purification of the residue by column chromatography, eluting with ethyl acetate-hexanes, provided 2.91 g (94%) of 43 as a colorless oil. $^1H$ NMR δ 1.28 (3H, t, J=7.1, $CH_3$), 3.18 (1H, d, J=6.7, OH) 4.27 (2H, q, J=7.1, $CH_2$), 4.37 (1H, dd, J=3.1, 6.7, CHOH), 4.84 (1H, d, J=3.1, PhCH), 7.4–7.5 (5H, m, Ph); $^{13}C$ NMR δ 171.84, 135.52 (quaternaries), 128.77, 128.71, 127.81, 73.87, 67.14, (CH), 62.37 ($CH_2$), 14.02 ($CH_3$); IR ($CHCl_3$) 3158, 2932, 2100, 1731, 1302, 1110 cm$^{-1}$.

Anal. Calcd. for $C_{11}H_{13}N_3O_3$; C,56.15; H,5.57; N, 17.87. Found: C,56.33; H,5.79; N,17.65.

A mixture of 1.88 g 43 (8.00 mmol) and 188 mg 10% Pd-carbon in 80 mL ethyl acetate was shaken under hydrogen (35 psi) for 14 hours. Filtration and concentration provided the crude amino alcohol 44 as a white power mp 69–71° C., which was used without purification. $^1H$ NMR δ 1.25 (3H, t, J=7.2, $CH_3$), 2.24 (3H, bs, OH and $NH_2$), 4.23 (2H, m, $CH_2$) 4.27 (2H, pp d, J=1.2, CH), 7.3–7.4 (m, 5H, Ph).

To 1.98 g(9.48)mmol of 44 and 2.98 g(10.43 mmol) sodium carbonate suspended in 57 mL 1:1 ether-water at 0° C. was added 1.35 mL (9.48 mmol) benzyl chloroformate. The mixture was stirred 30 min., the solvent was evaporated, and the residue partitioned between methylene chloride and water. The organic layer was dried (sodium sulfate) and concentrated to provide urethane 45 (91% yield from 43); mp 103–105° C. (methylene chloride-hexanes). $^1H$ NMR δ 1.25 (3H, t, J=6.9, $CH_3$), 3.30 (1H, bs, OH), 4.25 (2H, q, J=6.9, $CH_2CH_3$), 4.44 (1H, app s, CHOH), 5.03 (1H, 1/2 AB q, J=11.9, $CH_2Ph$), 5.07 (1H, 1/2 AB q, J=11.9, $CH_2Ph$), 5.28 (1H, app d, J=9.5, PhCH), 5.76 (1H, bd, J=9.5, NH), 7.3–7.4 (10H, m, Ph): $^{13}C$ NMR δ 172.66, 155.61, 138.90, 136.24 (quaternaries), 128.54 (double signal) 128.42, 128.02, 127.76, 126.70, 73.41, 66.93, (CH), 62.49, 56.42 ($CH_2$), 13.98 ($CH_3$); IR $CHCl_3$) 3520, 3440, 1730, 1260, 1095 cm$^{-1}$.

Alan. Calcd. for $C_{19}H_{21}NO_5$; C,66.45; H,6.17; N,4.08. Found: C,66.29; H,6.28; N,3.98.

To a solution of 6.78 g (19.8 mmol) urethane 45 in 79 mL dry THF at −68° C. was added dropwise and with stirring a solution of m-BuLi (1.6 M in hexane; 12.4 mL, 19.8 mmol). After 5 minutes, 3.89 mL (29.7 mmol) trichloroethoxymethyl chloride and 2.65 g (19.8 mmol) LiI were added. Subsequently, the mixture was allowed to warm to ambient temperature over 1 hour. The reaction mixture was then poured into 1N hydrochloric acid, extracted with methylene chloride, and the organic layer dried ($MgSO_4$) and concentrated. Purification of the residue by column chromatography, eluting with ethyl acetate-hexanes, provided 8.22 g (82%) 46 as a colorless oil. H NMR δ 1.23 (3H, t, J=7.2, $CH_3$), 3.16 (1H, 1/2 AB q, J=11.7, $CH_2CCl_3$), 3.63 (1H, 1/2 AB q, J=11.7, $CH_2CCl_3$), 4.20 (2H, m, $CH_2CH_3$), 4.52 (1H, bs, $CHCO_2Et$), 4.70 (1H 1/2 AB q, J=7.3, $OCH_2O$), 4.85 (1H, 1/2 AB q, J=7.3, $OCH_2O$), 5.04 (1H, 1/2 AB q, J=11.9, $CH_2Ph$), 5.08 (1H 1/2 AB q, J=11.9, $CH_2Ph$), 5.41 (1H, app bd, J-9.2, PhCH), 5.80 (1H, d, J=9.2, NH), 7.28–7.34 (10H, m, Ph): $^{13}C$ NMR δ 168.92, 155.24, 138.38, 135.98 (quaternaries), 128.31, 128.14, 127.77, 127.72, 127.60, 126.12, 95.86, 94.39, 79.02 (CH), 77.00, 66.65, 61.43, 56.05 ($CH_2$), 13.77($CH_3$); IR ($CHCl_3$) 3440, 2912, 1760, 1290, 1095 cm.$^{-1}$.

Anal. Calcd. for $C_{22}H_{24}Cl_3NO_6$: C,52.48; H,4.81; N,2.78. Found: C,52.33 H, 4.82; N,2.68.

A mixture of 494 mg (0.98 mmol) of 46 and 205 mg (4.88 mmol) lithium hydroxide monohydrate in 16.3 mL 3:1 methanol-water was stirred at room temperature for 2 h. The solvent was evaporated and the residue partitioned between methylene chloride and 1 N hydrochloric acid. The organic phase was dried (sodium sulfate) and concentrated to afford 458 mg (96%) of 28. Acid 28 was converted to its dicyclohexylammonium salt for elemental analysis, mp 133.5–136.0° C. (ether). $^1H$ NMR δ 3.17 (1H, 1/2 AB q, J=11.7, $OCH_2CCl_3$), 3.65 (1H, 1/2 AB q, J=11.7, $OCH_2CCl_3$), 4.60 (1H, m, $CHOC_2H$), 4.73 (1H, 1/2 AB q, J=7.3, $OCH_2O$), 4.89 (1H, 1/2 AB q, J=7.3, $OCH_2O$), 5.08 (1H, 1/2 AB q, J=11.9, $PhCH_2O$), 5.17 (1H, 1/2 AB q, J=11.9, $PhCH_2O$), 5.51 (1H, app bd, J=9.0 PhCH), 5.95 (1H, d, J=9.0, NH), 7.2–7.5 (10H, m, Ph); $^{13}$C NMR δ 171.94, 156.21, 138.48, 135.95, 96.14 (quaternaries), 128.75, 128.52, 128.16, 128.09, 126.40, 76.33, 56.28 (CH), 94.88, 79.51, 67.51 (CH$_2$); IR (CHCl$_3$) 3460, 3100, 2990, 2910, 1760, 1720, 1360, 1290, 1140, 1090, 1060, 1010 cm$^{-1}$.

Alan. Calcd. for C$_{34}$H$_{43}$Cl$_3$N$_2$O$_6$ (28 dicyclohexylamine): C,58.41; H,6.59; N,4.26, Found: C,58.65; H,6.51; N,4.17.

Baccatin III Ester 30: A mixture of 80 mg (0.105 mmol) 7, 301 mg (9.629 mmol) 28, 36 mhg (0.210 mmol) 4-(dimethylamino) pyridine, and 130 mg (0.629 mmol) dicyclohexylcarbondiimide in 5.25 mL toluene at 75° C. was stirred for 1 hour. The reaction mixture was cooled, filtered, and the filtrate washed with 0.5 N hydrochloric acid, water and dried (sodium sulfate). Concentration and purification of the residue by column chromatography, eluting with ethyl acetate-hexanes, provided 120 mg (94%) 30 as a colorless, amorphous solid. $^1$H NMR δ 1.10 (3H, s, C-17), 1.17 (3H, s, C-16), 1.77 (3H, s, C-19) 1.90 (3H, s, C-18), 1.9– 2.4 (3H, m, 1/2 C-6, C-14), 2.10 (3H, s, OAc), 2.39 (3H, s, OAc), 2.5–2.6 (1H, m, 1/2 C-6), 3.23 (1H, 1/2 AB q, J=11.4, OCH$_2$CCl$_3$), 3.63 (1H, 1/2 AB q, J=11.4, OCH$_2$CCl$_3$), 3.87 (1H, d, J=7.1, C-3), 4.13 (1H, 1/2 AB q, J=8.3 C-20), 4.26 (1H, 1/2 AB q, J=8.3, C-20), 4.58 (1H, 1/2 AB q, J=12.0, OCH$_2$CCO$_3$), 4.71 (1H, 1/2 AB q, J=7.3 OCH$_2$O), 4.82 (1H, 1/2 AB q, J=7.3, OCH$_2$O), 4.85–5.0 (4H, m, C-5, PhCH$_2$O, 1/2 OCH$_2$CCl$_3$), 5.42 (1H, br d, J=8.5 C-2'), 5.51 (1H, dd, J=7.1, 10.7, C-7), 5.61 (1H, d, J=7.1, C-2), 5.68 (1H, br d, J=9.1, C-3'), 6.22 (1H, t, J=6.7, C-13), 6.28 (1H, s, C-10), 7.1–7.4 (11H, m, Ph, NH), 7.45 (2H, app t, J=7.4, OBz), 7.55 (1H, app t, J=7.4, OBz), 8.06 (2H, app d, J=7.4, OBz).

A similar reaction performed with 7, 10 equivalents of 28, 10 equivalents of di-2-pyridyl carbonate, and 3.3 equivalents of 4-(dimethylamino)pyridine in toluene at 75° C. for 36 h provided 30 in 50% yield (78% based on recovered 7).

Baccatin III Ester 33: A mixture of 120 mg (0.0996 mmol) of 30 and 97 mg (1.49 mmol) Zn dust in 1.2 ML 1:1 acetic acid-methanol was sonicated 30 min. Additional zinc (65 mg; 0.996 mmol) was added and sonication continued for a total of 5 h. The solvent was decanted, the zinc and zinc salts rinsed with methanol, the organic phases combined, diluted with water, and extracted with methylene chloride. The methylene chloride layer was washed with water, dried (sodium sulfate), and concentrated. Chromatography of the residue, eluting with ethyl acetate-hexanes, provided 57–75 mg (65–85%) of 33. $^1$H NMR δ1.17 (3H, s, C-17), 1.27 (3H, s, C-16) 1.71 (3H, s, C-19), 1.83 (3H, s, C-18), 1.9–2.1 (3H, m, 1/2 C-6, C-1 4), 2.28 (3H, s, OAc), 2.43 (3H, s, OAc), 2.5–2.6 (1H, m, 1/2 C-6), 3.80 (1H, d, J-7.0, C-3), 4.20 (1H, 1/2 AB q, J=7.8, C-20), 4.32 (1H, 1/2 AB q, J=7.8, C-20), 4.4–4.5 (1H, m, C-7), 4.6–4.7 (1H, m, C-2'), 4.96 (1H, d, J=7.6, C-5), 4.98 (1H, 1/2 AB q, J=12.4, PhCH$_2$O), 5.10 (1H, 1/2 AB q, J=12.4, PhCH$_2$O), 5.39 (1H, br d, J=8.2, NH), 5.65–5.7 (2H, m, C-3', C-2), 6.26 (1Hm t, J=7.1, C-13), 6.29 (1H, s, C-10), 7.2–7.4, (10H, m, Ph), 7.53 (2H, t, J=7.4, OBz), 7.64 (1H, t, J=7.4, OBz), 8.15 (2H, d, J=7.4, OBz); $^{13}$C NMR δ 203.57, 172.47, 171.20, 170.28, 166.92, 155.81, 141.95, 138.07, 136.27, 133.17, 129.22, 81.17, 79.07, 58.60, 43.16 (quaternaries), 133.68, 130.23, 128.92, 128.68, 128.46, 128.25, 128.11, 127.66, 126.74, 84.40, 77.42, 75.54, 74.96, 73.52, 72.20, 45.58 (CH), 76.48, 66.97, 35.76, 35.59 (CH$_2$), 26.84, 22.61, 21.92, 20.82, 14.79, 9.57 (CH$_3$); UV [MeOH, wavelength $_{max}$ nm (ε)] 230 (22 000); HRFABMS Calcad. (M+Na) 906.3313, Obsvd. 906.3207.

Deprotection-Acylation of 33 to Give Taxol, Cephalomannine, and 34–39: A mixture of 242 mg (0.274 mmol) of 33, 42 μL trifluoroacetic acid, and 43 mg Pd black in 4 mL isopropanol was shaken under hydrogen (35 psi) for 1.5 h. Filtration and concentration of the filtrate afforded the corresponding ammonium trifluoroacetate, which was used without purification. To 20 mg (0.023 mmol) of this material and 2 mg 4-(dimethylamino)pyridine in 1.3 mL pyridine at ambient temperature was added dropwise and with stirring 0.028 mmol of the acylating agent. After 30 minutes, an additional 0.0184 mmol of the acylating agent was added, if necessary, and stirring was maintained another 30 min. The mixture was then diluted with methylene chloride, washed with 1N hydrochloric acid, water, and the organic phase was dried (sodium sulfate). Concentration and purification of the residue by column chromatography, eluting with ethyl acetatehexanes, provided a product that was chromatography, eluting with ethyl acetate-hexanes, provided a product that was chromatographically and spectroscopically pure.

Taxol

Prepared in 90% yield from benzoyl chloride to give material chromatographically and spectroscopically identical to an authentic sample.[29]

Cephalomannine

Prepared in 81% yield from tigloyl chloride to give material spectroscopically and chromatographically identical to an authentic sample.[29] HRMS (negative ion Cl; methane reagent gas) Calcd. (M) 831.3466, Obsvd. 831.3389.

Azido Taxol 34

Prepared in 71% yield from 4-azidobenzoyl chloride. $^1$H NMR δ1.13 (3H, s, C-17), 1.23 (3H, s, C-16), 1.67 (3H, s, C-19), 1.78 (cH, s, C-18), 1.9–2.1 (3H, m, 1/2 C-6, C-14), 2.22 (3H, s, OAc), 2.37 (3H, s, OAc), 2.45–2.55 (1H, m, 1/2 C-1 6), 3.79 (1H, d, J=6.9, C-3), 4.18 (1H, 1/2 AB q, J=8.2, C-20), 4.28 (1H, 1/2 AB q, J=8.2, C-20), 4.38 (1H, dd, J=6.8, 11.0, C-7), 4.75–4.8 (1H, m, C-2'), 4.92 (1H, d, J=7.6, C-5), 5.66 (1H, d, J=7.0, C-2), 5.76 (1H, dd, J=2.4, 8.8, C-3'), 6.22 (1H, t, J=8.2, C-13), 6.27 (1H, s, C-10), 6.98 (1H, app d, J=8.8, NH), 7.01 (2H, app d, J=8.6, N$_3$Ar), 7.3–7.5 (7H, m, Ph, OBz), 7.61 (1H, app t, J=7.4, OBz), 7.73 (2H, d, J=8.6, N$_3$Ar), 8.12 (2H, app d, J=7.4, OBz); $_{13}$CNMR δ 203.55, 172.76, 171.17, 170.36, 167.03, 165.96, 143.83, 141.87, 137.94, 133.20, 130.03, 129.15, 81.15, 79.04, 58.58, 43.16 (quaternaries), 133.70, 130.19, 129.00, 128.88, 128.70, 128.44, 128.35, 127.03, 119.07, 84.38, 75.54, 74.96, 73.18, 72.27, 72.14, 55.08, 45.67 (CH), 76.48, 35.63 (double signal) (CH$_2$), 26.84, 22.58, 21.77, 20.80, 14.79, 9.55 (CH$_3$); UV [MeOH, wavelength $_{max}$ nm (ε)] 230 (23 000), 270 (20 000); HRFABMS Calcd. (M+Na) 917.3221, Obsvd. 917.3236.

Trifluoromethyl Taxol 35

Prepared in 86% yield from 4-(trifluoromethyl) benzoyl chloride. $^1$H NMR δ 1.19 (3H, s, C17), 1.28 3H, s, C-16), 1.71 (3H, s, C-19), 1.81 (3H, s, C-18), 1.8–2.4 (3H, m, 1/2 C-6, C-14), 2.28 (3H, s, OAc), 2.44 (3H, s, OAc), 2.5–2.6 (1H, m, 1/2 C-6), 3.43 (1H, d, J=4.7, OH), 3.79 (1H, d, J=7.5, C-3, 4.19 (1H, 1/2 AB q, J=8.5, C-20), 4.31 (1H, 1/2 AB q, J=8.5, C-20), 4.35–4.45 (1H, m, C-7), 4.79 (1H, dd, J=2.4, 4.7, C-2'), 4.94 (1H, d, J=8.0, C-5), 5.67 (1H, d, J=7.0, C-2), 5.79 (1H, dd, J=2.4, 9.0, C-3'), 6.23 (1H, t, J=7.0, C-13), 6.27 (1H, s, C-10), 7.03 (1H, d, J=9.0, NH), 7.2–7.7 (10H, m, Ar), 7.84 (2H, app d, J=8.2, Ar), 8.13 (2H, app d, J=8.2, Ar); $_{13}$C NMR δ 203.51, 172.62, 171.25, 170.34, 167.05, 165.00, 141.77, 137.60, 136.92, 133.37, 129.15, 128.72, 128.46, 81.22, 79.09, 58.62, 43.18 (quaternaries), 133.77, 130.20, 129.11, 128.72, 128.54, 127.52, 127.01, 125.79, 84.37, 75.51, 74.89, 72.92, 72.47, 72.19, 55.02, 45.66, (CH), 77.91, 35.57 (double signal) (CH$_2$), 26.88, 22.63, 21.75, 20.84, 14.84, 9.54 (CH$_3$): UV [MeOh, wavelength $_{max}$ nm ($\epsilon$)] 230 (29 000); HRFABMS Calcd. (M+Na) 944.3081, Obsvd. 944.3022.

Bromo Taxol 36

Prepared in 76% yield from 4-bromobenzoyl chloride. $^1$H NMR δ 1.14 (3H, s, C-17), 1.24 (3H, s, C-16), 1.68 (3H, s, C-19), 1.78 (3H, s, C-18), 1.9–2.4 (3H, m, 1/2 C-6, C-14), 2.24 (3H, s, OAc), 2.38 (3H, s, OAc), 2.5–2.6 (1H, m. 1/2 C-6), 3.79 (1H, d, J=6.9, C-3), 4.19 (1H, 1/2 AB q, J=8.3, C-20), 4.31 (1H, 1/2 AB q, J=8.3, C-20), 4.40 (1H, dd, J=7.0, 11.1, C-7), 4.78 (1H, d, J=2.5, C-2'), 4.94 (1H, d, J=7.9, C-5), 5.67 (1H, d, J=6.9, C-2), 5.77 (1H, dd, J=2.5, 8.7, C-3'), 6.22 (1H, t, J=8.6, C-13), 6.26 (1H, s, C-10), 6.97 (1H, d, J=8.7, NH), 7.3–7.6 (12H, m Ar), 8.13 (2H, d, J=7.3, Ar); $^{13}$C NMR δ 203.57, 172.62, 171.28, 170.35, 167.01, 165.98, 141.86, 137.70, 133.19, 132.33, 128.46, 126.74, 81.13, 79.04, 58.59, 43.13 (quaternaries), 133.77, 131.92, 130.19, 129.08, 128.72, 128.62, 126.99, 84.35, 75.51, 74.85, 73.00, 72.39, 72.19, 54.94, 45.57, (CH), 76.58, 35.56, (double signal) (CH$_2$), 26.85, 22.62, 21.75, 20.86, 14.86, 9.53 (CH$_3$); HRFABMS Calcd. (M[$_{79}$Br]+H) 932.2493, Obsvd. 932.2577.

Acetyl Taxol 37

Prepared in 67% yield from 4-(acetyl) benzoyl chloride. $_1$H NMR δ 1.14 (3H, s, C-17), 1.24 (3H, s, C-16), 1.68 (3H, s, C-19), 1.77 (3H, s, C-18), 1.9–2.4 (3H, m, 1/2 C-6, C-14), 2.22 (3H, s, OAc), 2.38 (3H, s, OAc), 2.5–2.6 (1H, m, 1/2 C-6), 2.61 (3H, s, Ac), 3.79 (1H, d, J=7.3, C-3), 4.19 (1H, 1/2 AB q, J=8.6, C-20), 4.31 (1H, 1/2 AB q, J=8.6, C-20), 4.37 (1H, dd, J=6.6, 10.4, C-7), 4.79 (1H, d, J=2.1, C-2'), 4.94 (1H, d, J=7.0, C-5), 5.67 (1H, d, J=7.3, C-2), 5.76 (1H, dd, J=2.1, 7.1, C-3'), 6.23 (1H, t, J=7.9, C-13), 6.26 (1H, s, C-10), 7.05 (1H, d, J=7.1, NH) 7.3–7.65 (8H, m, Ar), 7.82 (2H, app d, J=8.3, Ar), 7.97 (2H, app d, J=8.3, Ar), 8.13 (2H, d, J=7.3, Ar); $^{13}$C NMR δ 203.56, 197.33, 172.61, 171.28, 170.36, 167.00, 166.02, 141.80, 139.48, 137.65, 137.41, 133.22, 128.50, 81.14, 79.02, 58.57. 43.13, (quaternaries), 133.77, 130.02, 129.18, 129.08, 128.72, 128.66, 127.37, 127.01, 84.35, 75.51, 74.85, 73.01, 72.39, 72.18, 55.02, 45.60, (CH), 77.20, 35.58, (double signal) (CH$_2$), 26.84, 22.63, 21.74, 20.87, 14.86, 14.18, 9.54, (CH$_3$); UV [MeOH, wavelength $_{max}$ nm ($\epsilon$)] 236 (37 000); HRFABMS Calcd. (M+H) 896.3493, Obsvd. 896.3536.

Benzoyl Taxol 38

Prepared in 66% yield from 4-(benzoyl)benzoyl chloride. $^1$H NMR δ 1.14 (3H, s, C-16), 1.23 (3H, s, C-17), 1.68 (3H, s, C-19), 1.79 (3H, s, C-18), 2.23 (3H, s, OAc), 2.3–2.4 (2H, m, C-14), 2.38 (3H, s, OAc), 2.4–2.6 (2H, m. C-6), 3.67 (1H, d, J=5.2, OH), 3.79 (1H, d, J=7.0, C-3), 4.18 (1H, 1/2 AB q, J=8.4, C-20), 4.30 (1H, 1/2 AB q, J=8.4, C-20), 4.35–4.42 (1H, m, C-7), 4.80 (1H, dd, J=5.2, 2.6, C-2'), 4.94 (1H, d, J=7.8, C-5), 5.66 (1H, d, J=7.0, C-2), 5.80 (1H, dd, J=8.9, 2.6, C-3'), 6.24 (1H, t, J=7.5, C-13), 6.27 (1H, s, C-10), 7.18 (1H, bd, J=8.9, NH), 7.3–7.6 (5H, m, Ph), 7.61 (2H, t, J=7.2, OBz), 7.7–7.9 (5H, m, OBz, Ar), 8.12 (2H, d, J=7.2, OBz); $^{13}$C NMR δ203.56, 195.86, 172.65, 171.25, 170.35, 166.96, 166.20, 141.81, 140.44, 137.70, 136.77, 133.18, 81.12, 78.99, 77.42, 77.00, 58.53, 43.13, (quaternaries), 133.74, 132.99, 130.17, 130.13, 130.07, 129.05, 128.70, 128.44, 127.04, 127.02, 84.34, 77.20, 75.50, 74.85, 73.03, 72.32, 72.14, 55.06, 45.61, (CH), 76.57, 35.57, (double signal) (CH$_2$), 26.83, 22.61, 21.75, 20.85, 14.84, 9.54, (CH$_3$): UV [MeOH, wavelength $_{max}$ nm ($\epsilon$)] 232 (28 000), 258 (27 000); HRFABMS Calcd. (M+H) 958.3650, Obsvd. 958.3591.

Hydroxy Taxol 39

Prepared in 51% yield from salicylic acid N-hydroxysuccinimide ester. $^1$H NMR δ 1.14 (3H, s, C-17), 1.22 (3H, s, C-16), 1.68 (3H, s, C-19), 1.76 (3H, s, C-18) 2.23 (3H, s, OAc), 2.3–2.4 (2H, m, C-14), 2.35 (3H, s, OAc), 2.4–2.6 (2H, m, C-6), 3.78 (1H, d, J=7.0, C-3), 4.19 (1H, 1/2 AB q, J=8.4, C-20), 4.29 (1H, 1/2 AB q, J=8.4, C-20), 4.37 (1H, dd, J=10.4, 6.6, C-7), 4.80 (1H, d, J=2.5, C-2'), 4.93 (1H, d, J=8.2, C-5), 5.65 (1H, d, J=7.0, C-2), 5.79 (1H, dd, J=8.6, 2.5, C-3'), 6.22 (1H, bt, J=9.6, C-13), 6.26 (1H, s, C-10), 6.86 (1 H, t, J=7.6, Ar), 6.93 (1H, bd, J=8.6, NH), 7.3–7.5 (10H, m, Ar, OBz), 7.63 (1H, t, J=7.4, OBz), 8.09 (2H, d, J=7.4, OBz); $^{13}$C NMR δ 203.50, 172.27, 171.27, 170.40, 169.49, 166.90, 161.51, 141.57, 137.51, 133.33, 129.02, 113.68, 81.23, 78.85, 58.57, 43.08, (quaternaries), 134.72, 133.83, 130.03, 129.07, 128.71, 128.51, 126.93, 125.62, 118.91, 118.70, 84.30, 75.51, 74.77, 73.01, 72.32, 72.18, 54.32, 45.66, (CH), 76.47, 35.61, (double signal) (CH$_2$), 26.81, 22.61, 21.56, 20.85, 14.90, 9.51 (CH$_3$); UV [MeOH, wavelength $_{max}$ nm ($\epsilon$)] 232 (28 000), 300 (5 000); Fluorescence MeOH, wavelength $_{max(300\ nm\ excitation)}$ nm] 342, 410; HRFABMS Calcd. (M+H) 870.3337, Obsvd. 870.3354.

Deprotection-Acylation of 33 to Give 10-Acetyl TAXOTERE® AND 34

A protocol for they hydrogenolytic deprotection (16 h) and acylation of 33 similar to that described above was followed, except that the acylations were conducted at ambient temperature.

10-Acetyl TAXOTERE®

Prepared in 94% yield from di-t-butyldicarbonate to give material with spectroscopic parameters identical to those reported.[12] HRFABMS Calcd. (M+H) 850.3650, Obsvd. 850.3687.

Azido Taxol 34

Prepared in 79% yield from 4-azidobenzoic acid N-hydroxysuccinimide ester and excess ammonium salt.

From the foregoing, this invention therefore contemplates certain intermediates and taxol analogs, of the following structures:

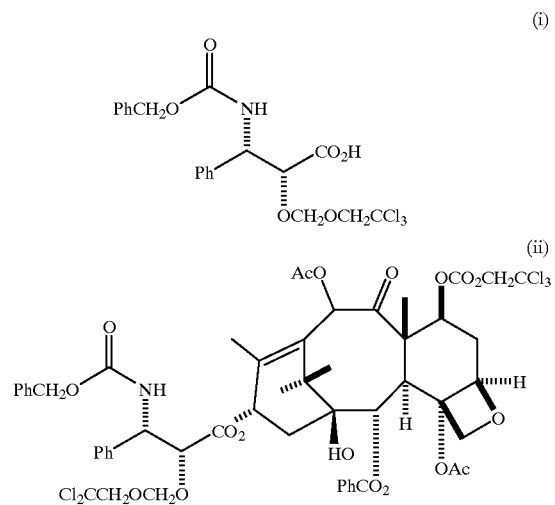

-continued

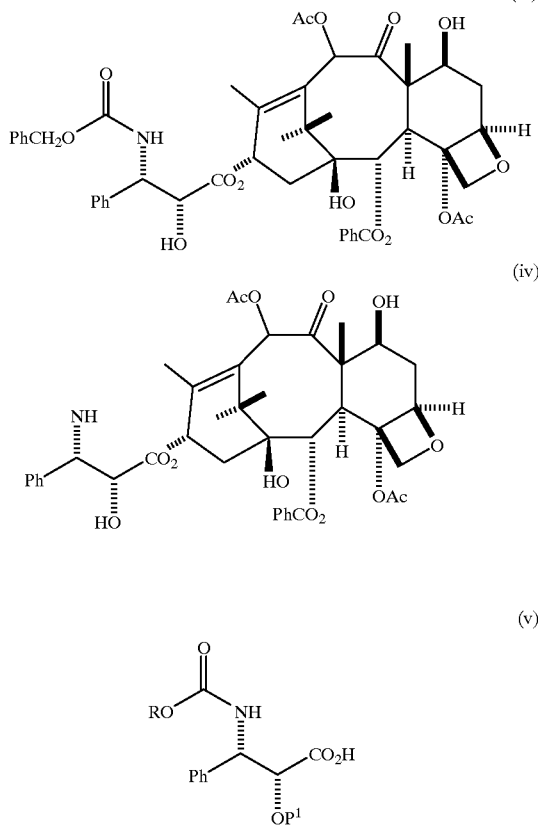

(iii)

(iv)

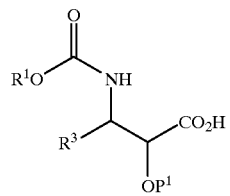

(v)

R¹=alkyl, olelinic, or aromatic group
P¹=hydroxyl-protective group
R¹≠(CH₃)₃C

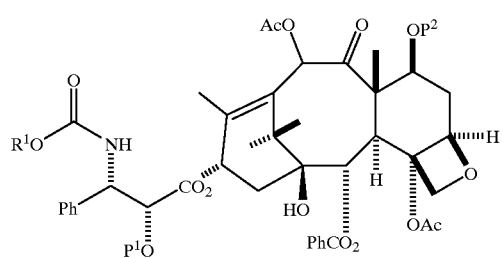

(vi)

R¹=alkyl, olelinic, or aromatic group
R³=hydrogen, alkyl, olelinic, or aromatic group
P¹=hydroxyl-protecting group (vii)

R¹=alkyl, olelinic, or aromatic group
P¹=hydroxyl-protecting group

P²=hydroxyl-protecting group

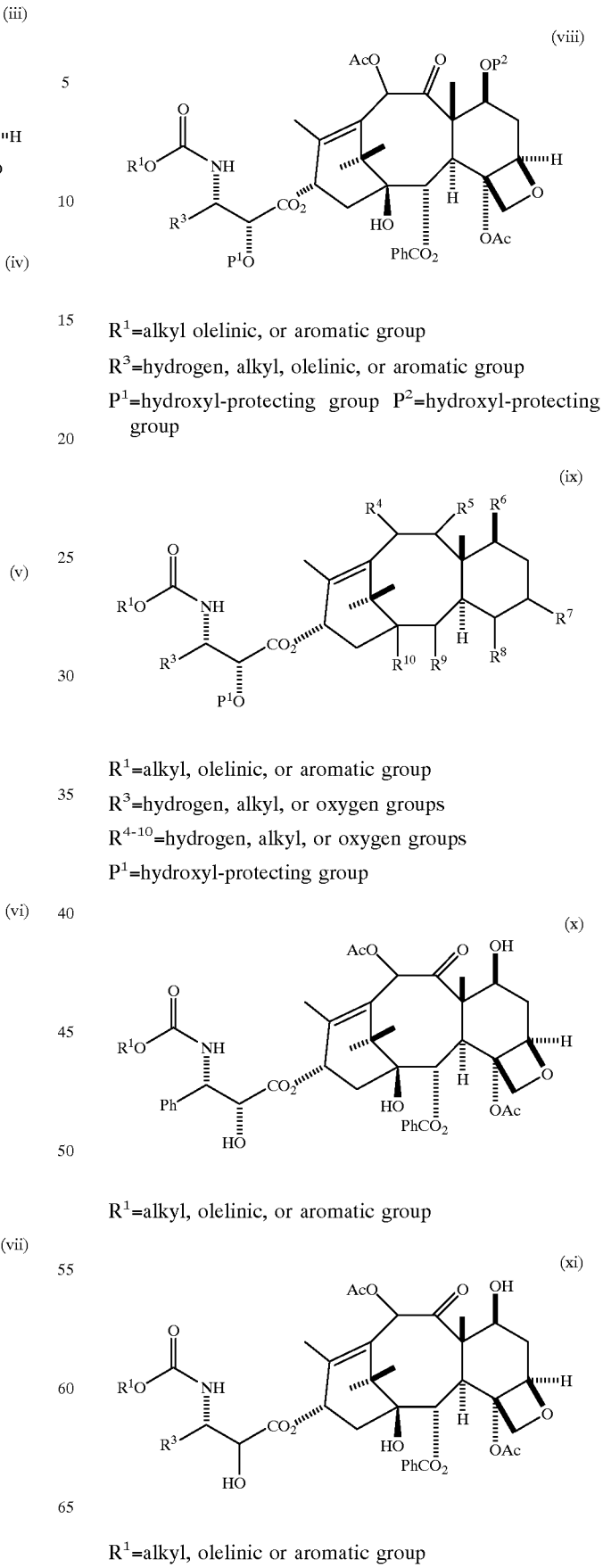

(viii)

R¹=alkyl olelinic, or aromatic group
R³=hydrogen, alkyl, olelinic, or aromatic group
P¹=hydroxyl-protecting group  P²=hydroxyl-protecting group (ix)

R¹=alkyl, olelinic, or aromatic group
R³=hydrogen, alkyl, or oxygen groups
R⁴⁻¹⁰=hydrogen, alkyl, or oxygen groups
P¹=hydroxyl-protecting group (x)

R¹=alkyl, olelinic, or aromatic group (xi)

R¹=alkyl, olelinic or aromatic group $R^2$=hydrogen, alkyl, olelinic or aromatic group

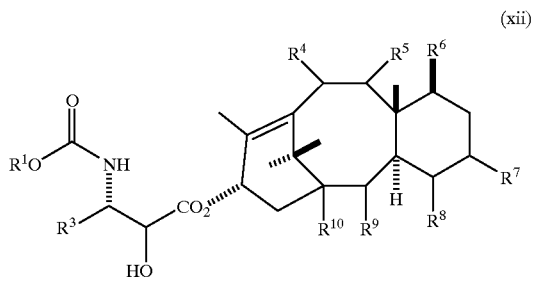
(xii)

$R^1$=alkyl, olenic, or aromatic group
$R^3$=hydrogen, alkyl, olelinic, or aromatic group
$R^{4-10}$=hydrogen, alkyl, or oxygen groups

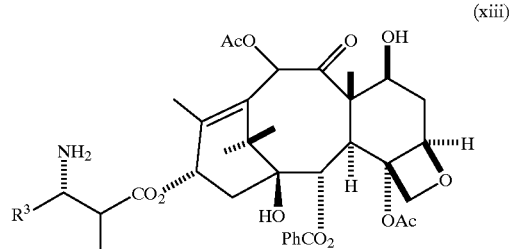
(xiii)

$R^3$ = hydrogen, alkyl, olelinic, or aromatic group

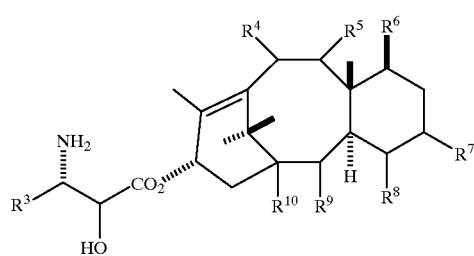
(xiv)

$R^3$ = hydrogen, alkyl, olelinic, or aromatic group
$R^{4-10}$ = hydrogen, alkyl, or oxygen groups Without further elaboration the foregoing will so fully illustrate our invention that others may, by applying current or future knowledge, adapt the same for use under various conditions of service.

What is claimed is:

1. A chemical process useful for the production of taxol analogs and their intermediates, comprising:

condensing a compound of the general formula:

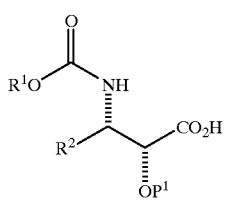

with a taxane of the general formula:

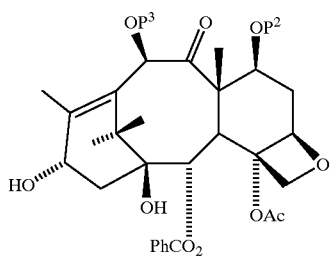

to give a first intermediate of the general formula:

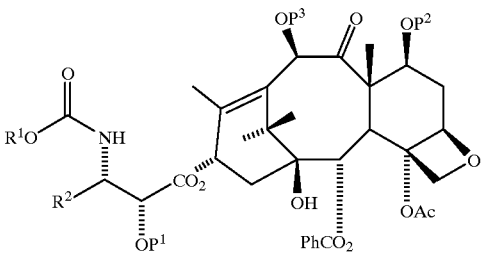

wherein $R^1$=an olefinic group, an aromatic group or $PhCH_2$
$R^2$=hydrogen or Ph
$P^1$=a hydroxyl protecting group
$P^2$=a hydroxyl protecting group
$P^3$=a hydroxyl protecting group or $COCH_3$.

2. The chemical process according to claim 1 including the step of deprotecting the first intermediate to give a second intermediate of the general formula

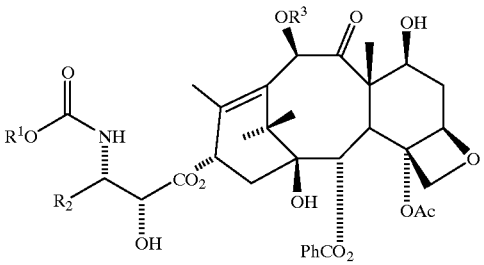

wherein $R^1$=an olefinic group, an aromatic group or $PhCH_2$
$R^2$=hydrogen or Ph
$R^3$=hydrogen or $COCH_3$.

3. The chemical process according to claim 2 including the step of deprotecting the second intermediate to give a third intermediate of the general formula

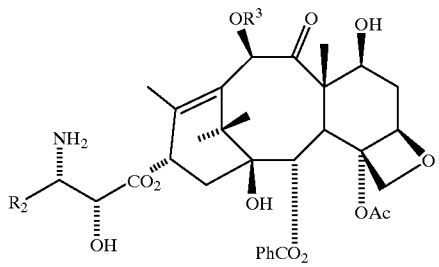

wherein

R² = hydrogen or Ph

R³ = hydrogen or COCH₃.

4. The chemical process according to claim 3 including the step of N-acylation of the third intermediate to form a taxol analog of the general formula

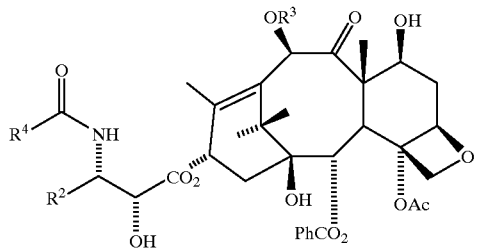

wherein

R² = hydrogen or Ph

R³ = hydrogen or COCH₃

R⁴ = an alkyl group, an olefinic group, an aromatic group, hydrogen, or an oxygen, nitrogen or sulfur group.

5. A process for the preparation of taxol analogs comprising the following steps:

(a) substituting protective groups OP² or OP³ for the hydroxyl groups at C-7 and C-10, respectively, of 10-deacetylbaccatin III to form a first intermediate having the formula

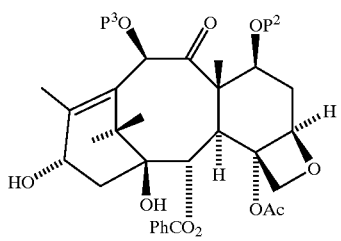

wherein P² and P³ are each $CO_2CH_2CCl_3$ or another hydroxyl-protecting group;

(b) condensing the first intermediate formed in step (a) with

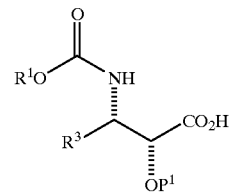

wherein R¹ is an alkyl, benzyl, olefinic, or aromatic group or PhCH₂, R³ is hydrogen or Ph and P¹ is an hydroxyl-protecting group to form a second intermediate having a formula

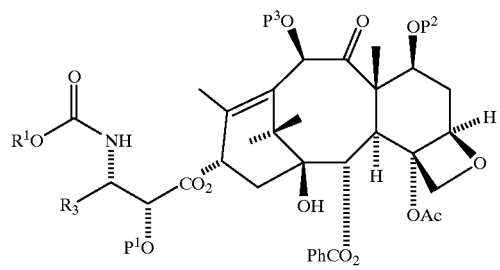

wherein R¹ is an alkyl, benzyl, olefinic, or aromatic group or PhCH₂, R³ is hydrogen or Ph, and P¹, P² and P³ are hydroxyl-protecting groups;

(c) deprotecting the hydroxyl groups for the P¹, P² and P³ protecting groups at C2', C-7 and C-10, respectively, of the second intermediate formed in step (b) to form a product having a formula

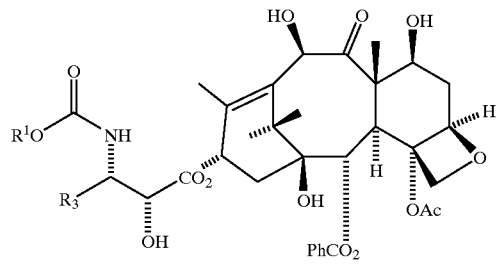

wherein R¹ is an alkyl, benzyl, olefinic or aromatic group or PhCH₂ and R³ is hydrogen or Ph;

(d) deprotecting the product of step (c) at C3' to form a third intermediate of the general formula

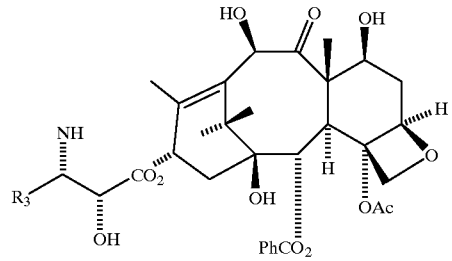

wherein R³ is hydrogen or Ph; and (e) acylating the third intermediate at the C3' nitrogen site to form

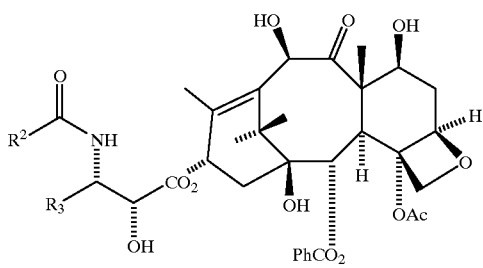

wherein $R^2$ is hydrogen, or an alkyl, olefinic, aromatic, oxygen, nitrogen, or sulfur group and $R^3$ is hydrogen or Ph.

6. The process according to claim 5 wherein $R^3$ is Ph.

7. The process according to claim 5 wherein $R^3$ is hydrogen.

8. The process according to claim 5 wherein $P^1$ is selected from a group consisting of $CO_2CH_2CCl_3$ and $CH_2OCH_2CCl_3$.

9. The process according to claim 5 wherein $P^2$ is selected from a group consisting of $CO_2CH_2CCl_3$ and $CH_2OCH_2CCl_3$.

10. The process according to claim 5 wherein $P^3$ is selected from a group consisting of $CO_2CH_2CCl_3$ and $CH_2OCH_2CCl_3$.

11. The process according to claim 5 wherein at least one of $P^1$, $P^2$, and $P^3$ is $CO_2CH_2CCl_3$.

12. The process according to claim 5 wherein $R^3$ is hydrogen and $R^1$ is $PhCH_2$.

13. The process according to claim 5 wherein $R^3$ is hydrogen and $R^2CO$ is selected from a group consisting of 4-azidobenzoyl, 4-(trifluoromethyl)benzoyl, 2-naphthoyl, hexanoyl, pivaloyl, cyclohexylcarbonyl, and 1-adamantylcarbonyl.

14. The process according to claim 5 wherein $R^3$ is Ph and $R^2CO$ is selected from a group consisting of tigloyl, 4-azidobenzoyl, 4-(trifluoromethyl)benzoyl, 4-bromobenzoyl, 4-(acetyl)benzoyl, 4-(benzoyl)benzoyl, and salicyl.

15. A chemical process useful for the production of taxol analogs and their intermediates, comprising:

condensing a compound of the general formula:

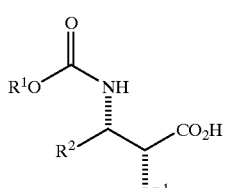

with a taxane of the general formula:

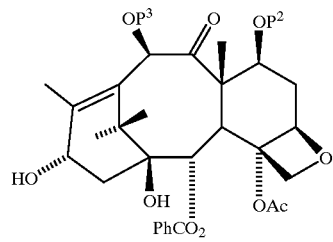

to give a first intermediate of the general formula:

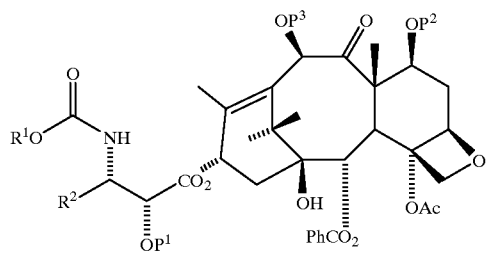

wherein $R^1$=an olefinic group, an aromatic group or $PhCH_2$ $R^2$ an alkyl group, an olefinic group, or an aromatic group $P^1$=a hydroxyl protecting group $P^2$=a hydroxyl protecting group $P^3$=a hydroxyl protecting group or $COCH_3$.

16. The chemical process according to claim 15 including the step of deprotecting the first intermediate to give a second intermediate of the general formula

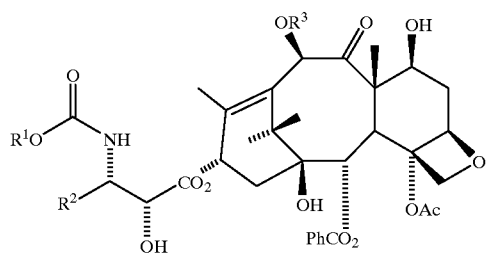

wherein $R^1$=an olefinic group, an aromatic group or $PhCH_2$ $R^2$=an alkyl group, an olefinic group, or an aromatic group $R^3$=hydrogen or $COCH_3$.

17. The chemical process according to claim 16 including the step of deprotecting the second intermediate to give a third intermediate of the general formula

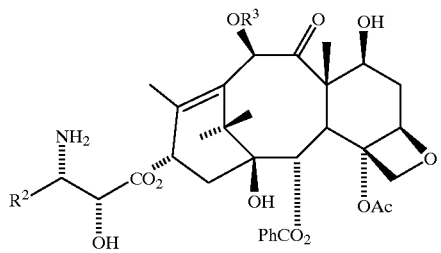

wherein $R^2$=an alkyl group, an olefinic group, or an aromatic group $R^3$=hydrogen or $COCH_3$.

18. The chemical process according to claim 17 including the step of N-acylation of the third intermediate to form a taxol analog of the general formula

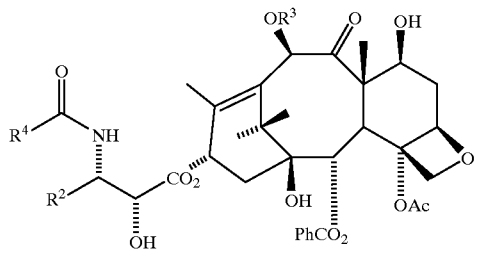

wherein $R^2$=an alkyl group, an olefinic group, or an aromatic group $R^3$=hydrogen or $COCH_3$ $R^4$=an alkyl group, an olefinic group, an aromatic group, hydrogen, or an oxygen, nitrogen or sulfur group.

19. A process for producing a compound useful in the production of taxol, taxol analogues and their intermediates comprising the steps of:

(a) acylating a first compound having a formula:

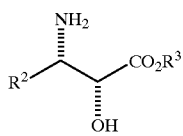

wherein $R^2$=an alkyl group, olefinic group, an aromatic group, hydrogen or Ph $R^3$=an alkyl group at the C3 nitrogen to form a second compound having a formula:

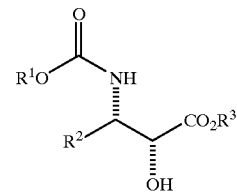

wherein $R^1$=an olefinic group, an aromatic group or $PhCH_2$
$R^2$=an alkyl group, olefinic group, an aromatic group, hydrogen or Ph
$R^3$=an alkyl group;

(b) protecting the C2 hydroxyl of the second compound with a hydroxyl protecting group to form a third compound having a formula:

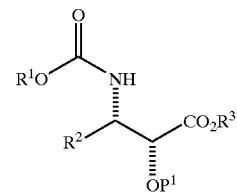

wherein $R^1$=an olefinic group, an aromatic group or $PhCH_2$
$R^2$=an alkyl group, olefinic group, an aromatic group, hydrogen or Ph
$R^3$=an alkyl group
$P^1$=a hydroxyl protecting group; and (c) saponifying the third compound to form a fourth compound having a formula:

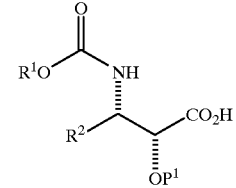

wherein $R^1$=an olefinic group, an aromatic group or $PhCH_2$
$R^2$=an alkyl group, olefinic group, an aromatic group, hydrogen or Ph
$P^1$=a hydroxyl protecting group.

20. A process according to claim 19 wherein $R^3$ is an ethyl group.

21. A process according to claim 19 wherein $R^2$ is selected from a group consisting of hydrogen and Ph.

22. A process according to claim 21 wherein $R^2$ is Ph.

23. A process according to claim 21 wherein $R^1$ is $PhCH_2$.

24. A process according to claim 19 wherein $P^1$ is selected from a group consisting of $CO_2CH_2CCl_3$ and $CH_2OCH_2CCl_3$.

* * * * *